United States Patent
Restrepo et al.

(10) Patent No.: US 9,474,611 B2
(45) Date of Patent: Oct. 25, 2016

(54) COST-EFFECTIVE METHOD FOR MANUFACTURING METAL CRANIAL PROSTHESES

(75) Inventors: Mauricio Toro Restrepo, Sabaneta (CO); David Sierra Navaro, Sabaneta (CO); Balmore Bedoya Henao, Sabaneta (CO)

(73) Assignee: INDUSTRIAS MEDICAS SAMPEDRO S.A. (CO)

(*) Notice: Subject to any disclaimer, the term of this patent is extended or adjusted under 35 U.S.C. 154(b) by 228 days.

(21) Appl. No.: 14/364,875

(22) PCT Filed: Dec. 14, 2011

(86) PCT No.: PCT/IB2011/055684
§ 371 (c)(1),
(2), (4) Date: Sep. 18, 2014

(87) PCT Pub. No.: WO2013/088206
PCT Pub. Date: Jun. 20, 2013

(65) Prior Publication Data
US 2015/0018949 A1    Jan. 15, 2015

(51) Int. Cl.
A61F 2/28    (2006.01)
A61F 2/30    (2006.01)

(52) U.S. Cl.
CPC ...... *A61F 2/2875* (2013.01); *A61F 2002/3096* (2013.01); *A61F 2002/30784* (2013.01); *A61F 2002/30952* (2013.01); *Y10T 29/49885* (2015.01); *Y10T 29/49996* (2015.01)

(58) Field of Classification Search
CPC ............ Y10T 29/4998; Y10T 29/49982; Y10T 29/49885; B29C 43/183; B29C 43/18; B29C 2043/185; B29C 67/0051; B29C 70/30; B29C 2793/009; A61F 2/2875; A61F 2002/30952; A61F 2002/3096; G05B 2219/45168
See application file for complete search history.

(56) References Cited

U.S. PATENT DOCUMENTS

| 6,932,842 B1 | 8/2005 | Litschko et al. |
| 2002/0173854 A1 | 11/2002 | Amrich |

(Continued)

FOREIGN PATENT DOCUMENTS

| CN | 101264035 A | 9/2008 |
| CN | 101354579 A | 1/2009 |
| WO | 2008/034924 A1 | 3/2008 |

OTHER PUBLICATIONS

Written Opinion for PCT/IB2011/055684; 6 pgs.

(Continued)

*Primary Examiner* — Jermie Cozart
(74) *Attorney, Agent, or Firm* — Schmeiser, Olsen & Watts, LLP

(57) ABSTRACT

The present invention relates to a method for manufacturing an implantable prosthesis, in other words, a biomodel, which can be implanted in a patient, preferably in the cranium of a patient. The method is based on the use of commercially available adhesive tape, in order to reduce the manufacturing costs of said implant since there is no need to heat same to very high temperatures in order to mold the material to be implanted. The implant is preferably made of titanium via a cold-production process, which requires initially supplying a rapid prototype from a CAD model that corresponds to a plastic mold, which is covered with commercially available adhesive tape, in order to obtain another model that makes it possible to form the model that will be transferred to titanium, thus reducing the ideal temperature for molding same.

8 Claims, 2 Drawing Sheets

(56) References Cited

U.S. PATENT DOCUMENTS

Figure 1:
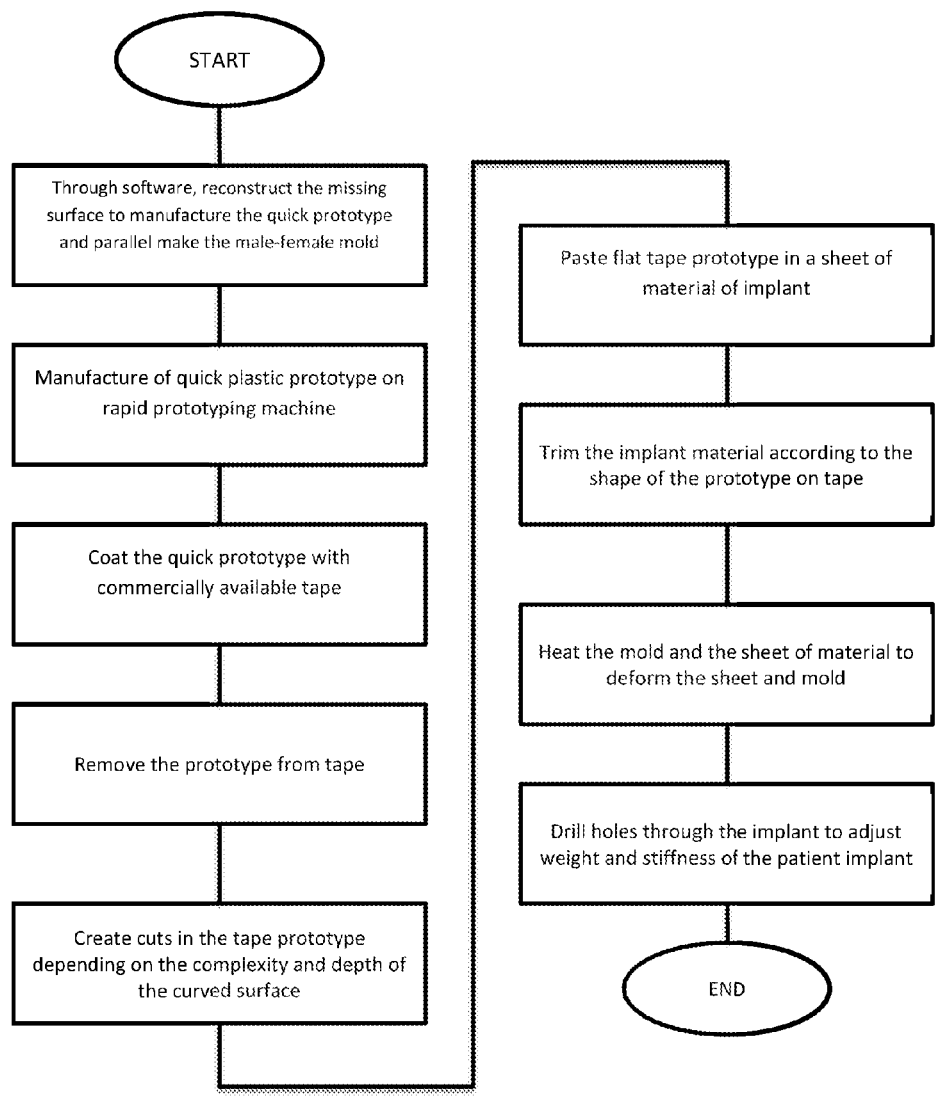

2003/0109784 A1 6/2003 Loh et al.
2004/0258732 A1 12/2004 Shikinami
2005/0133955 A1 6/2005 Christensen
2010/0292963 A1 11/2010 Schroeder
2011/0016690 A1 1/2011 Narainasamy et al.

OTHER PUBLICATIONS

International Preliminary Report on Patentability for PCT/IB2011/055684; 7 pgs.

COST-EFFECTIVE METHOD FOR MANUFACTURING METAL CRANIAL PROSTHESES

CROSS-REFERENCE TO RELATED APPLICATIONS

This application claims priority to PCT Application No. PCT/IB2011/055684, having a filing date of Dec. 14, 2011, the entire content of which are hereby incorporated by reference.

FIELD OF TECHNOLOGY

The present invention relates to a process for manufacturing an implantable prosthesis, i.e. a biomodel, which can be implanted in a patient, preferably in the skull of a patient, wherein the process is based on the use of commercially available tape, in order to reduce costs in the manufacture of said implant avoiding the need to heat the material to a very high temperature to mold it. The implant is preferably made in titanium after a cold production process, which requires initially a rapid prototyping of a CAD (Computer-Aided Design) model. The model corresponds to a plastic mold which is coated on commercially available adhesive tape. The adhesive tape is used in order to obtain another model which allows for the formation of a new model that will be made with titanium. The tape reduces the temperature required for molding the material. Thus, a very high temperature is not required to desirably shape the final implant in titanium.

BACKGROUND

There are a plurality of methods or processes for the manufacture of prostheses to be implanted in a patient suffering from a defect in the bone structure, mainly in the region of the skull. The defect may be due to a birth defect or surgical procedure, usually used when carrying out the removal of cancerous tumors that require removing a portion of both brain or surrounding skull.

In this regard, currently all methods or processes for the manufacture of such implants, which are mainly made of titanium because of the rigidity and maneuverability of the material, include steps that require very high temperatures. Manufacturing temperatures are typically higher than 450° C., to carry out the molding of the material adapted to a prescribed form of the prosthesis to be implanted by means of a pair of male and female molds which give it the desired shape.

However, this process is not entirely desirable given that in order to bend and shape the material, i.e. titanium, it is required that the molds reach very high temperatures. High temperatures increase the costs of production and operation, due to energy consumption, wherein such costs are directly transferred to the patient requiring the procedure.

Moreover, processes existing in the state of the art have a high environmental impact. Every time it is desired to perform a implant procedure it is also required to create a prosthesis to be implanted that, as noted above. This requires a very high operating temperatures and the power consumption is very high as well.

Thus, there are a number of disclosures focused on methods or processes for the manufacture of prostheses to be implanted in a patient, especially in the head thereof. Document EP 1457214 relates to an implant material comprising a porous article of a bioactive organic-inorganic, degradable and absorbable complex and a method for manufacturing such an article. The implant material comprises a porous article previously mentioned, in which a bioactive bioceramics powder is uniformly dispersed in a biodegradable and bioabsorbable polymer, and wherein it has continuous pores and the bioceramics powder is partly exposed at the inner surface of the pore.

The method described in this document is focused on the production of an implant material comprising a porous article of the organic-inorganic complex. In the method, a fabric-like fiber aggregate tissue is formed from a mixed solution prepared by dissolving a biodegradable polymer and bioabsorbable in a volatile dissolvent and dispersing a bioactive bioceramics powder therein. This is formed in a mold of porous fiber aggregate molding by compression thereof, the fiber aggregate molding is immersed in the volatile dissolvent, and then said dissolvent is removed.

However, the disclosure in this document has a major disadvantage which is based on the use of a number of solvents and dissolvents in order to process the porous fiber aggregate with a number of bioactive bioceramics corresponding to the material in which the prosthesis or implant is made. This makes the process described therein very complex and requires special equipment and elements which increase the costs of producing the implant itself.

On the other hand, document MXPA 03010379 discloses a method for the manufacture or production of a surgical mesh and plate implant, which comprises the steps of a) applying a masking to the two faces of a metal sheet, b) ablating selective masking on the sides of the foil but leaving an open hole for a screw, c) fixing a first tape to cover the first side and the masking on this, d) fixing a second tape to cover the second side and masking thereon, e) recording the acid portion of the screw hole to form a first side hole, f) removing the first film, g) acid recording the hole and other exposed portions of the first side, h) removing the second strip, i) acid recording the hole and other exposed portions of the second face, and j) removing the remaining masker.

However, just like in the document EP 1457214 previously defined, this requires specific steps of various materials that increase the costs of production of the implant using this process, taking into consideration the application of a masking of the surfaces of the sheet material in which the implant is made.

Document CN 101264035 mentions a method for the production or preparation of a titanium mesh cranial prosthesis. The method is characterized in that the image of the thin layer scanning CT is introduced in the region of two-dimensional coordinates. A midfield line, a baseline, a reference line and a plurality of brain construction lines are drawn. Reference sites of the skull to be repaired are determined at the intersection of each construction line and the fine skull in the symmetric region of the defect region; and the corresponding points of the prosthesis element is generated in the region of the skull defect; the image layer corresponding to the scan point element, the number of construction lines and the vertical distance between the point and the line item are recorded. Each sheet of film in different CT layers are entered in the coordinate region in order to carry out the operation to form the data of all points of the elements of cranial morphology in the defect region; and the titanium mesh is pressed according to multipoint data element points, to obtain the titanium mesh cranial prosthesis.

However, this document is mainly focused on software and method steps that are necessary to obtain a model of titanium mesh prosthesis to be implanted, from the software, which is not desirable in manufacturing an affordable and accessible prosthesis for any type of patient. However, production costs are very high, since they are linked directly with the software and licenses that manufacturers wish to supply. This is a disadvantage since it does not have availability at all times of the process but depends on the availability of the software to create the prototype of the implant.

Finally, document CN 101354579 relates to a method for obtaining a titanium alloy for defective human bone prosthesis by embossing mold, wherein the method provides a titanium alloy prosthesis bone having a high accuracy and meets the requirements of an individual patient for patients with bone defects and especially in those with complex defective bone structures. The method comprises the step of constructing a curved surface of the defective bone prosthesis according to the CT DICOM data format or MR DICOM data format of the patient's bone, where a titanium plaque mold is designed according to the curvature of the surface, and then the mold data are introduced into a digital tool control machine. Thus, a sealed mold needing design is machined by the machine-tool and in the titanium plate is accomplished by forming the mold pattern.

Accordingly, the data format DICOM CT or MRI DICOM data format of the patient's bone is subjected to 3D reconstruction, and a picture of the reconstructed bone is inserted into the digital control machine tool, and the digital control machine manufactures a bone prosthesis, and then a test is made between a bone prosthesis and a model of the patient's bone to ensure that the prosthesis is fully matched with the patient's skull.

However, the method described in this document, although it is very novel by including the use of a system for collecting and analyzing data for the prosthesis that best suits the patient, is carried out by known techniques for casting and to get the desired shape to a titanium plate, which in turn requires very high temperatures of operation in order to bend the titanium molds into the desired shape which, as indicated above, increases the costs of operation and affects the environment due to the high power consumption.

Thus, it is evident that there is a need in the state of the art to implement a process for manufacturing a prosthesis to be implanted in a patient, especially in the skull area, wherein the process uses commercially available and inexpensive elements to reduce operating costs and thereby enable more people to access this kind of surgical procedures to overcome a drawback, either congenital or obtained by the removal of cancerous tumors, which also requires the process to be eco-friendly by reducing the operating temperature, whereby electric power consumption is reduced.

SUMMARY

The process or method for manufacturing or obtaining an implantable prosthesis on a patient of the present invention comprises the following stages or steps:
- rendering out a CAD (Computer-Aided Design) design of the bone part to be implanted;
- manufacturing the male and female molds with the desired shape of implant, depending the body part where it is to be placed in the patient, from the design made in the previous step;
- manufacturing a quick prototype on a quick prototyping machine, wherein said prototype corresponds exactly with the final implant and the part is completed in plastic;
- coating the prototype with adhesive tape adopting the shape of the implant, wherein said coating can have at least one layer of tape, depending on the thickness of said tape;
- removing the adhesive tape from the prototype obtaining thereby another prototype with the same shape of the final implant;
- depending on the curvature of the implant to be produced, performing or not at least a straight cut in the prototype made in adhesive tape, in order to allow said tape to become completely flat, thereby creating a flat template, depending on the complexity and depth of the curved surface;
- placing the flat template with cuts in a sheet of material to manufacture the implant to be placed in the patient;
- trimming the sheet of material of the implant according to the flat template shape of the adhesive tape;
- preheating the male and female molds and the sheet of implantable material to a temperature not higher than 450° C.;
- introducing the cut implant material sheet between male and female molds and apply pressure until reaching the shape printed by the mold;
- removing the deformed plate from the mold that corresponds to the prosthesis to be implanted;
- creating round holes in the implantable material at the inner ends of each cut;
- polishing the edges of the implant to prevent inconvenience in the surgical procedure; and
- drilling the implant as desired in order to provide the stiffness, mass and desired permeability thereof according to the patient's bone structure.

BRIEF DESCRIPTION

FIG. 1 is a flowchart describing the process for manufacturing the prosthesis or implant of the present invention.

Figure 2:
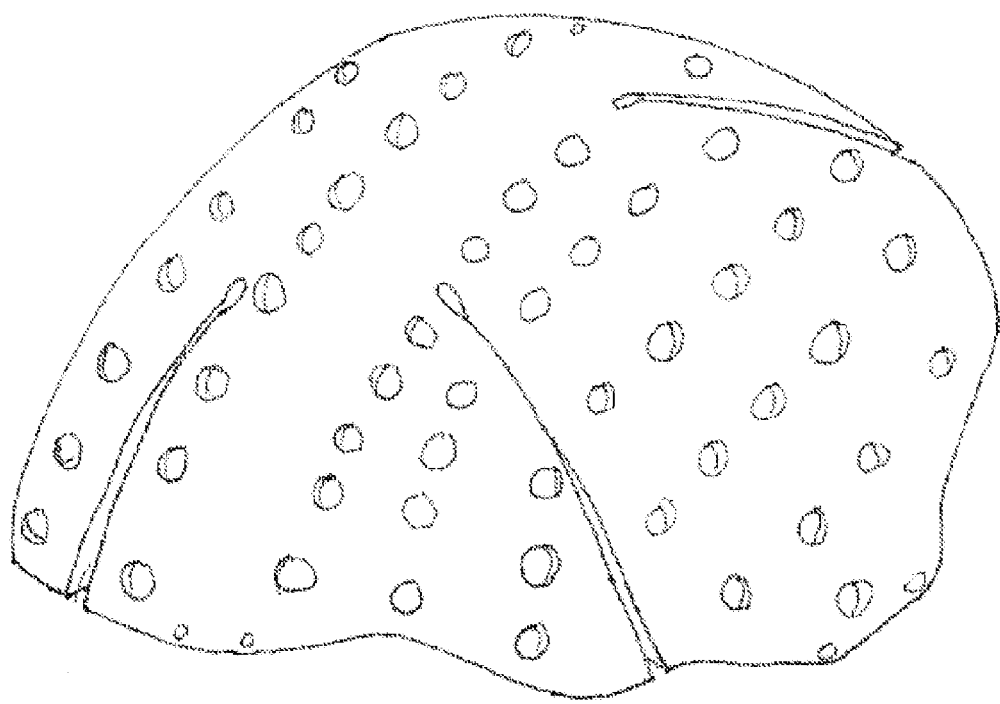

FIG. 2 corresponds to a perspective view of the implantable prosthesis obtained through the process shown in FIG. 1.

DETAILED DESCRIPTION OF THE INVENTION

An initial quick prototype is obtained with which the work will begin in order to obtain the final implant, wherein said quick prototype is manufactured in any plastic material, preferably ABS Acrylonitrile butadiene styrene, considering that plastic can be deformed at a temperature lower than the one required to deform a metal, such as titanium. Likewise, the quick prototype is carried out in a rapid prototyping machine commercially available.

Now, once the prototype in plastic is obtained, this is coated with any type of commercially available adhesive tape, in order to obtain a first implant on tape to be the basis for the manufacture in the final implant material. Thus, this plastic prototype must be tape coated, whereby at least one glued layer is disposed, in order to prevent the tape prototype from sagging when said layers of tape are removed from the plastic prototype and so the exact shape of the prosthesis to be implanted is obtained, which adapts to the patient and corresponds to the CAD design originally made.

Once these tapes are removed from the plastic prototype, a tape implant is obtained which can be maneuvered much more easily than the one obtained with the metal material in which the final implant is manufactured. Thus, the tape prototype requires, optionally depending on the curvature of the implant, at least one cut that is made from the outside towards the inside. This simulates a radius that does not reach the center of the implant, where the amount of cuts or holes depend on the complexity and depth of the curved surface. This step of creating cuts or holes is performed considering that the tape prototype is required to be flattened without being deformed, in order to place it on the metal foil on the implant. This ensures that the shape of the final implant to be placed in the patient accurately corresponds with the design created in the CAD program and can be placed on the patient.

In an embodiment of the invention, the sheet of material to manufacture the implant is a metal foil, such as pure titanium grade 4, which has a thickness in the range from 0.5 mm to 3.0 mm, preferably 0.8 mm, in order to have sufficient rigidity to be bent and manipulated before being implanted in the patient.

This sheet is cut by any metal cutting technique, specifically those used with titanium, which is known in the state of the art, wherein the cut of this sheet corresponds exactly to the shape of flattened tape prototype, including internal cuts and holes made on said tape.

Once the implant material is trimmed and the same shape of the tape prototype is achieved, it is necessary to obtain the desired shape of the implant to the implant material sheet cut, which takes place in the male and female molds, which are heated to a temperature that allows the desired bend and shape sheet metal, particularly pure titanium, as indicated above.

Accordingly, taking into account the temperature at which the metal to be implanted can be easily bent and handled, the male and female molds having the shape of the implant made through the design program as initially stated, said molds are preheated so the material can be heated to a temperature not higher than 450° C. and proceeds to join the molds with the metal sheet placed between said molds, in order to obtain the desired shape for said sheet and thereby to obtain the final implant.

In this regard, once the sheet metal material to be implanted has the shape of the desired implant and is adjusted to the bone shape of the patient, it is important to take into consideration the stiffness, mass and permeability of the patient's bone structure, since the implant is to be set to such properties that are unique to each patient. Thus, in order to achieve the desired stiffness, mass and permeability, a series of holes in the bent sheet metal are made, which can are also useful as anchor points for sutures and so the process of implementing the prosthesis in the patient can be finished.

In addition, the path of the holes in the implant is an important feature, since these help with the permeability and heat dissipation that may hold the implant and for a weight reduction as well, i.e. so the patient does not notice the implant in his/her daily routine.

Finally, the implant is finished by an etching process, which corresponds to a surface treatment used to remove metal impurities such as blemishes, contaminants, rust, etc. and finally there is a step of anodizing the metal foil, i.e. the final implant.

The invention claimed is:

1. A process for manufacturing or producing an implantable prosthesis for implanting in a patient, comprising the following steps:
rendering out a CAD design to implement a bony part;
manufacturing a male mold and a female mold with a desired implant shape, depending on a body part where is to be placed in the patient;
manufacturing a quick prototype on a rapid prototyping machine, wherein said quick prototype corresponds exactly with a final implant, the quick prototype comprised of plastic;
coating the quick prototype with an adhesive tape taking a shape of the final implant, wherein said coating has at least one layer of tape;
removing the adhesive tape from the quick prototype thus obtaining a tape prototype with the same shape as the final implant;
performing at least one straight cut into the tape prototype made of the adhesive tape, depending on the complexity and depth of the curved surface;
creating a plurality of round holes at the inner ends of each cut of the tape prototype to then flatten said tape prototype and obtain a flat template;
capturing the flat template of tape in a sheet of material to manufacture the implant;
trimming the sheet material of the implant according to the shape of the flat template made on adhesive tape;
preheating the male mold and the female mold and the sheet at a specific temperature for heating an implantable metal;
introducing the implant material sheet cut between the male mold and the female mold and apply pressure until reaching the shape printed by the mold;
removing a deformed plate from the mold corresponding to the prosthesis to be implanted;
polishing the edges of the implant to prevent disruption to a surgical procedure; and
drilling the implant according to the properties of stiffness, weight and permeability of a patient's bone structure.

2. The process of claim 1, wherein the quick prototype initially obtained is made of any plastic material.

3. The process of claim 1, wherein the sheet of material to manufacture the implant is a sheet of biocompatible metal.

4. The process of claim 3, wherein the metal is titanium.

5. The process of claim 3, wherein the implant material sheet has a thickness in the range from 0.5 mm to 3.0 mm, preferably 0.8 mm.

6. The process of claim 1, further comprising the step of performing a stripping process to remove impurities, the impurities including blemishes, contaminants, and rust.

7. The process of claim 1, further comprising the step of anodizing the final implant.

8. A process for making an implantable prosthesis in a patient, comprising:
rendering out a CAD design to implement a bony part;
manufacturing a male mold and a female mold with a desired implant shape, depending on a body part where is to be placed in the patient;
providing a prototype;
coating the prototype with an adhesive tape taking a shape of an implant, wherein said coating has at least one layer of tape;
creating a plurality of round holes at the inner ends of each cut of the tape prototype to then flatten said tape prototype and obtain a flat template;
removing the adhesive tape from the prototype;
developing a template from the adhesive tape;
making an implantable prosthesis from the template;
polishing the edges of the implant; and
drilling the implant according to the properties of stiffness, weight and permeability of a patient's bone structure.

* * * * *